United States Patent [19]

Levine et al.

[11] Patent Number: 4,594,165

[45] Date of Patent: Jun. 10, 1986

[54] METHOD OF ENHANCING SEPARATION OF ABNORMALLY LIGHT RED CELLS FROM GRANULOCYTES IN A CENTRIFUGED BLOOD SAMPLE

[76] Inventors: Robert A. Levine, 31 Pilgrim La., Guilford, Conn. 06437; Stephen C. Wardlaw, 128 Sunset Hill Dr., Branford, Conn. 06405

[21] Appl. No.: 671,934

[22] Filed: Nov. 16, 1984

[51] Int. Cl.⁴ .............................................. B01D 21/26
[52] U.S. Cl. .................................... 210/767; 210/789; 210/927
[58] Field of Search ............... 210/789, 927, 645, 767; 422/101, 44, 46; 73/53, 61.1 R, 149; 494/37

[56] References Cited

U.S. PATENT DOCUMENTS

| | | |
|---|---|---|
| 3,750,645 | 8/1973 | Bennett et al. ..................... 210/787 |
| 3,960,727 | 6/1976 | Hochstrasser ...................... 210/117 |
| 4,027,660 | 7/1977 | Wardlaw et al. .................... 210/927 |
| 4,082,085 | 4/1978 | Wardlaw et al. .................... 210/789 |
| 4,159,896 | 7/1979 | Levine et al. ....................... 210/789 |
| 4,181,609 | 1/1980 | Wardlaw et al. .................... 210/789 |

Primary Examiner—Richard V. Fisher
Assistant Examiner—Sharon T. Cohen
Attorney, Agent, or Firm—William W. Jones

[57] ABSTRACT

In order to provide for a sharply defined line of demarcation between red cells and granulocytes in a centrifuged blood sample, the blood sample is drawn into a capillary tube. The bottom of the capillary tube is capped and the blood sample is centrifuged for a time sufficient to layer the blood sample in its constituent blood cell types. The capillary tube is then removed from the centrifuge and the top of the capillary tube is capped. The tube is then placed in the centrifuge inverted from its original orientation whereupon the sample is centrifuged again. Abnormally light red cells are thus trapped towards the bottom of the red cell column whereupon they cannot float up into the granulocyte band.

4 Claims, 3 Drawing Figures

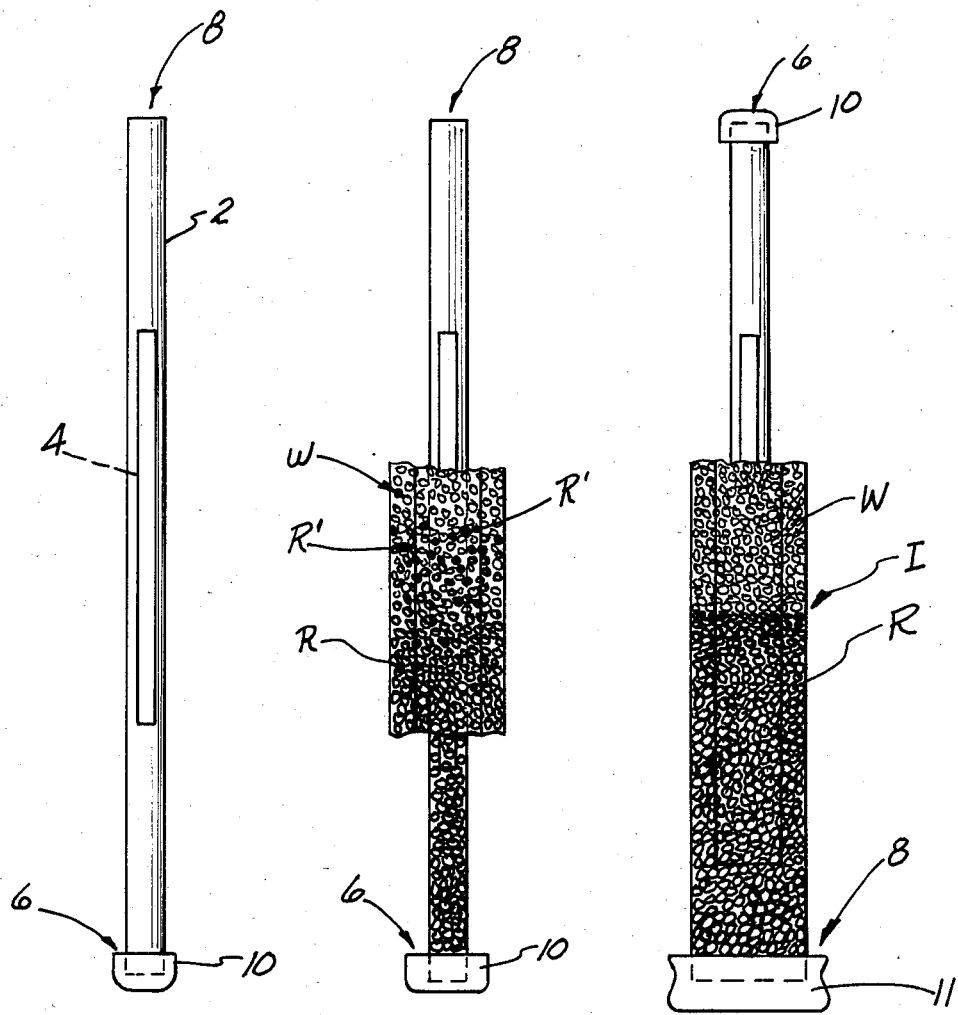

METHOD OF ENHANCING SEPARATION OF ABNORMALLY LIGHT RED CELLS FROM GRANULOCYTES IN A CENTRIFUGED BLOOD SAMPLE

This invention relates to a method for clarifying the interface between the red cell layer and the granulocyte layer in a centrifuged blood sample.

U.S. Pat. Nos. 4,027,660 issued Apr. 2, 1976; and 4,082,085 issued Apr. 4, 1978 relate to a technique for performing differential white cell counts in a sample of anticoagulated blood which has been drawn into a capillary tube and centrifuged. A generally cylindrical float is disposed in the capillary tube. The float will settle into the red cell layer during centrifugation and extend through the white cell and platelet layer or buffy coat so as to physically elongate the white cell platelet layers. A stain such as acridine orange is used to differentially color the different cell types which constitute the buffy coat so that the buffy coat appears as a plurality of different color bands in the capillary tube. The layering of the cells according to density during centrifugation allows cell counts to be made by measuring the distance between the boundaries of each cell band.

U.S. Pat. Nos. 4,159,896 issued July 3, 1979; and 4,181,609 issued Jan. 1, 1980 describe a problem, and a solution therefor, which is encountered in some blood samples tested in accordance with the above-described technique. The problem is a poorly defined demarcation between the top of the centrifuged column of red cells and the bottom of the centrifuged column of granulocytes. The interface between these two cell layers may be blurry or poorly defined because of the fact that the blood sample may contain abnormally light red cells which will rise up into the lower portion of the granulocyte layer after centrifugation, or will not be centrifuged down into the red cell mass in the first place. The solution to this problem is to add potassium oxalate to the blood sample to densify the red cells so that the abnormally light red cells will settle down into the red cell layer during centrifugation and will stay there. In order to accentuate the densification, the blood sample is warmed while in the capillary tube prior to centrifugation. Following this prior art procedure, satisfactory delineation of the red cell-granulocyte boundary is achieved in about 98% of normal outpatient cases and in about 70% of hospitalized patients. In view of the ineffectiveness of the prior art procedures in a significant number of cases, particularly in the hospital environment, it is apparent that a more efficacious procedure would be useful so that good red cell-granulocyte separation would be achieved in virtually all samples.

We have determined that a relatively simple procedure will ensure a clear interface between the red cells and the granulocytes. In the process of this invention, the potassium oxalate is added to the blood sample in the effective amount of 400 to 600 mg/dl, as taught by the prior art. Heating of the sample in the capillary tube may be performed but is not necessary. One end of the capillary tube is capped and the sample is centrifuged toward the capped end of the tube. Centrifugation is continued until the red cells and white cells are separated from the plasma and form two adjacent layers. The other end of the capillary tube is then capped and the sample is then centrifuged again toward the other capped end of the tube. This causes the red cells to shift from one end of the tube to the other end while the white cells and plasma also shift positions. The abnormally light red cells which were on the top of the red cell column adjacent the white cells after the first centrifugation are trapped on the bottom of the red cell column at the end thereof furthest from the white cells after the second centrifugation. In order to return to the interface between the red cell column and the white cell column, these light red cells have to percolate through the red cell column, an occurrence which is rare due to the natural stickiness of the red cells. Rather than being able to return to the red cell-white cell interface, the abnormally light red cells tend to adhere to other heavier red cells as the light red cells try to rise through the red cell column. It should be noted that the normal zeta potential of the red cells is overcome in the initial centrifugation so that, as a result of the initial centrifugation, the red cells tend to stick together to a certain degree to form clumps of several cells. This stickiness is the result of the presence of naturally occurring macromolecules on the red cells. In contrast, the white cells are not as sticky and will readily pass through the red cell column when the blood sample is recentrifuged. This technique has been found to be effective in a substantial number of outpatient and hospital cases where a single centrifugation with potassium oxalate and heating did not produce a satisfactory, well defined red cell-white cell interface.

It is, therefore, an object of this invention to provide a method for obtaining a clear, well defined red cell-white cell interface in a centrifuged sample of anticoagulated whole blood.

It is an additional object of this invention to provide a method of the character described wherein abnormally light red cells are prevented from rising into the white cell layer.

It is a further object of this invention to provide a method of the character described wherein the abnormally light red cells are caused to migrate to the bottom of the centrifuged red cell column.

It is another object of this invention to provide a method of the character described which includes centrifugation of the blood sample in a capillary tube followed by reverse re-centrifugation of the blood sample in the capillary tube.

These and other objects and advantages of the method of this invention will become more readily apparent from the following detailed description of the invention taken in conjunction with the accompanying drawings, in which:

FIG. 1 is a side elevational view of a capillary tube, cap, float test combination used to perform the method of this invention;

FIG. 2 is a side elevational view, partially enlarged of the testing paraphenalia after a blood sample has been centrifuged once therein; and FIG. 3 is a view similar to FIG. 2 but showing the blood sample after the same has been reverse re-centrifuged.

Referring now to the drawings, there is shown in FIG. 1 the blood testing paraphenalia used in this invention. The equipment includes a transparent capillary tube 2 in the bore of which there is disposed a substantially cylindrical plastic body 4. The opposite ends of the tube 2 are designated 6 and 8 for purposes of reference. After a blood sample has been drawn into the tube 2, the end 6 is closed off with a plastic cap 10. The blood sample in the tube will have been treated with potassium oxalate so as to increase the density of the red cells as described in the aforementioned prior art. After the sample has been drawn into the tube 2 and the cap 10 affixed in place, the tube 2 is centrifuged so as to pack the red cells R in a column bottoming out at the capped end 6 of the tube 2. If the interface between the red cells R and the white cells W is poorly defined and blurry because of abnormally light red cells R' residing in the white cell layer W, then an additional cap 11 is added to the end of the tube 2. The tube 2 is inverted and then placed in the centrifuge and centrifuged again, this time to move the packed red cells R toward the capped end 8 of the tube 2. During the initial centrifuging step, the red cells R will pack together and tend to stick together due to the presence of the naturally occurring macromolecules on the red cells and the overcoming of the normal zeta potential of the red cells. During the second inverted or reverse centrifugation step, this agglutination of the red cells remains so that the agglutinated red cells move as a relatively coherent mass toward the end 8 of the tube, which was previously occupied by plasma. The abnormally light red cells R' are thus pushed ahead of the agglutinated red cells toward the end 8 of the tube 2. During this reverse centrifugation, it is very difficult for the abnormally light red cells R' to move back through the agglutinated red cells R due to the stickiness of the latter. The white cells W, on the other hand, are not sticky and will easily pass through the red cell column to reassume their position above the red cells R, as shown in FIG. 3. The result is a well defined interface between the red cells R and the white cells W, as shown in FIG. 3.

It will be readily appreciated that the process of this invention will increase the instances of well defined red cell-white cell interfaces in the prior art centrifuged capillary tube blood testing procedures. The process is easy to perform, does not add to the cost of the test, and only slightly increases the time needed to perform the test.

Since many changes and variations of the disclosed embodiment of the invention may be made without departing from the inventive concept, it is not intended to limit the invention otherwise than as required by the appended claims.

What is claimed is:

1. A method for forming an interface of increased clarity between red cells and white cells in a centrifuged sample of anticoagulated blood, said method comprising the steps of:
   (a) drawing a sample of anticoagulated blood into a capillary tube;
   (b) closing one end of said capillary tube;
   (c) centrifuging said blood sample in said capillary tube so as to cause red cells in said sample to aggregate at said one end of said capillary tube;
   (d) closing the opposite end of said capillary tube;
   (e) inverting said sample, and re-centrifuging so as to cause said aggregated red cells to migrate toward said opposite end of said capillary tube in a column.

2. The method of claim 1 wherein said blood sample is anticoagulated with potassium oxalate.

3. A method for forming an interface of increased clarity between red cells and white cells in a centrifuged sample of anticoagulated blood, said method comprising the steps of:
   (a) providing a sample of anticoagulated blood in a capillary tube;
   (b) closing one end of said capillary tube;
   (c) centrifuging said blood sample in said capillary tube so as to cause red cells in said blood sample to aggregate at said one end of said capillary tube in a column with the heaviest of the red cells at the bottom of the column and the lightest of the red cells at the top of the column;
   (d) closing the opposite end of said capillary tube;
   (e) inverting said capillary tube and re-centrifuging to move said red cell column toward said opposite end of said capillary tube whereby the lightest of the red cells are confined towards said opposite end of said capillary tube by heavier aggregated red cells to prevent the lightest of the red cells from mingling with white cells at the red cell-white cell interface.

4. The method of claim 3 wherein said blood sample is anticoagulated with potassium oxalate.

* * * * *